United States Patent [19]

Schattschneider

[11] Patent Number: 4,599,146
[45] Date of Patent: Jul. 8, 1986

[54] LONG TERM CURRENT DEMAND CONTROL SYSTEM

[75] Inventor: George K. Schattschneider, Victoria, Canada

[73] Assignee: Her Majesty the Queen in right of Canada, as represented by the Minister of National Defence of Her Majesty's Canadian Government, Ottawa, Canada

[21] Appl. No.: 674,739

[22] Filed: Nov. 26, 1984

[30] Foreign Application Priority Data

Dec. 22, 1983 [CA] Canada ................................. 444172

[51] Int. Cl.$^4$ ............................................. G01N 27/46
[52] U.S. Cl. ...................................... 204/1 T; 204/404
[58] Field of Search ................. 204/1 C, 147, 404, 196

[56] References Cited

U.S. PATENT DOCUMENTS

| 4,138,323 | 2/1979 | Statsenko et al. | 204/196 |
| 4,155,814 | 5/1979 | Tejfalussy et al. | 204/1 T |
| 4,196,055 | 4/1980 | Lennox, Jr. | 204/1 T |

Primary Examiner—Aaron Weisstuch
Attorney, Agent, or Firm—William R. Hinds

[57] ABSTRACT

A Long Term Current Demand Control System which can be used in corrosion research is disclosed. The system is used to potentiostatically control several cathodes at several different set potentials. All cathodes can be placed in the same test tank and draw current from a single anode.

4 Claims, 4 Drawing Figures

LONG TERM CURRENT DEMAND CONTROL SYSTEM

This invention relates to current measuring instruments for multiple-potential, multiple-cathode potentiostatic testing.

Of prime importance in the area of corrosion research is the testing of long term current demand (LTCD). Basically, the LTCD testing involves the determination of the long term current requirements of various metal plates as they are maintained electronically at a number of set potentials while immersed in an electrolyte. The metal plates, usually called cathodes or working electrodes, are immersed in a test tank filled with sea water. The set potentials at which the cathodes are maintained are referenced to a silver/silver chloride reference electrode. With the information gained from the LTCD tests, corrosion scientists are able to make significant contributions to the optimization of the parametric specification of equipment used for cathodic protection of ships.

The potentiostat, in its various forms of electronic realization, is the heart of both old and new LTCD control systems and is undoubtedly the single most important test and measurement instrument of the corrosion scientist. A potentiostat is used to control the potential between a working electrode (cathode) and a reference electrode by automatically varying the current between the working electrode (cathode) and counter electrode (anode) in a three electrode system.

Basically, all potentiostatic systems consist of a potentiostat which takes a set potential and a reference potential as its inputs. The reference electrode is buffered so that a negligible current is drawn from it. The output of the potentiostat is a current which flows through the anode, the electrolyte and finally the grounded cathode. This produces a potential drop between the reference electrode and the cathode which is equal to the set potential. Demand current measurement can take place at either the anode or the cathode in a single cathode system; however, a nonintrusive measurement method has to be used.

Difficulty arises in the prior art because corrosion tests often require months and even years to complete. Furthermore, a large number of different materials must be tested and each material must be tested at a number of different potentials. Obviously, experiments of such long duration should be carried out concurrently. However, this requires the use of a large number of potentiostats which would be prohibitively expensive if commercial units were used. Furthermore, all cathodes must be placed in the same test tank to ensure that they all experience the same relative conditions such as temperature, salinity, and sea water (electrolyte) flow rate. It is also desirable that, since a single test tank is used, a single large anode should serve as the current source for all the cathodes.

It is necessary, on occasion, to use a plurality of potentiostats to test a number of cathodic materials at different set potentials within a single test tank. In such a system, since all the reference electrodes are at the same relative potential it is quite impossible to test a number of cathodes at different set potentials if the cathodes are all grounded together.

Commercial corrosion measurement systems such as Princeton Applied Research Models 173 and 350A are very accurate and extremely flexible, but are expensive and not designed to control potentiostatically more than one cathode at a time.

The prior art solved the problem by using inexpensive potentiostats electronically isolated or "floated" with respect to each other. If, for example, the requirement was to test at six different set potentials, six separate potentiostats would be used and the ground point of each would be purely a local ground and not a system ground. However, the prior art required that there be a separate, floating power supply for each potentiostat. The necessity of multiple power supplies is a very inefficient and undesirable requirement.

Furthermore, the method used to take cathodic current readings in the prior art is both intrusive and awkward. All cathodes controlled by a single potentiostat are connected to a common local ground. To take a reading, a low-value precision resistor is inserted in series between the cathode and ground. The voltage drop across the resistor is measured with a differential or floating voltmeter and the current is calculated using Ohm's law. It is clear that, as well as being awkward, the introduction of the resistor into the current path introduced an unnecessary, and not always insignificant, error.

The present invention provides a novel method to achieve potentiostatic control. In the present LTCD system the cathode is ungrounded and "draws" the ionizing current from a fixed potential anode. The potentiostat designs up until now "drove" the ionizing current through the variable potential anode to the grounded cathode. Using the approach of the present invention, it is possible to achieve a multiple-potential, multiple-cathode potentiostatic control system which requires only two power supplies: one to offset the anode to some fixed potential and one to supply the power requirements for the LTCD system electronics. It was found that the new design approach makes it a simple matter to provide potentiostatic current control to each cathode individually.

In addition, the new system is smaller, lighter, more efficient, less expensive, more accurate, and easier to set up than prior art systems. Using the present invention the system can potentiostatically control, for example, sixty cathodes at twelve different set potentials in blocks of five cathodes per set potential.

It is one object of the present invention to provide a method of measuring long term current demand in metal plate cathodes to determine parameters of cathodic protection for each plate. The plate cathodes form part of an electrical circuit in an apparatus. The apparatus has an anode and a reference electrode wherein the anode, reference electrode, and cathodes are immersed in an electrolyte. The method comprises the steps of: applying a fixed potential to the anode; measuring a reference potential at the reference electrode; and drawing a current directly through said cathodes from said anode by means of a potentiostatic control. The potentiostatic control is responsive to an established set potential and an established reference potential at the reference electrode. The algebraic difference between the set potential and the reference potential causes a variation of the current drawn from the cathode which is indicative of corrosive action affecting the cathode.

It is another object of the present invention to provide an apparatus for measuring long term current demand in metal plate cathodes to determine parameters of cathodic protection for each plate. The plate cathodes form part of an electrical circuit having an anode and a reference electrode wherein the anode, reference electrode, and cathodes are immersed in an electrolyte. The apparatus comprises: means to apply a fixed potential to said anode; and potentiostatic control means operable to draw current directly through the cathode from the anode in the electrolyte. The potentiostatic control is responsive to an established set potential and an established reference potential at the reference electrode, wherein the algebraic difference between the set potential and the reference potential causes a variation of the current drawn from the cathode which is indicative of corrosive action affecting the cathode.

These and other features and advantages of this invention will become apparent from the detailed description below. That description is to be read in conjunction with the accompanying drawings in which.

Figure 1:
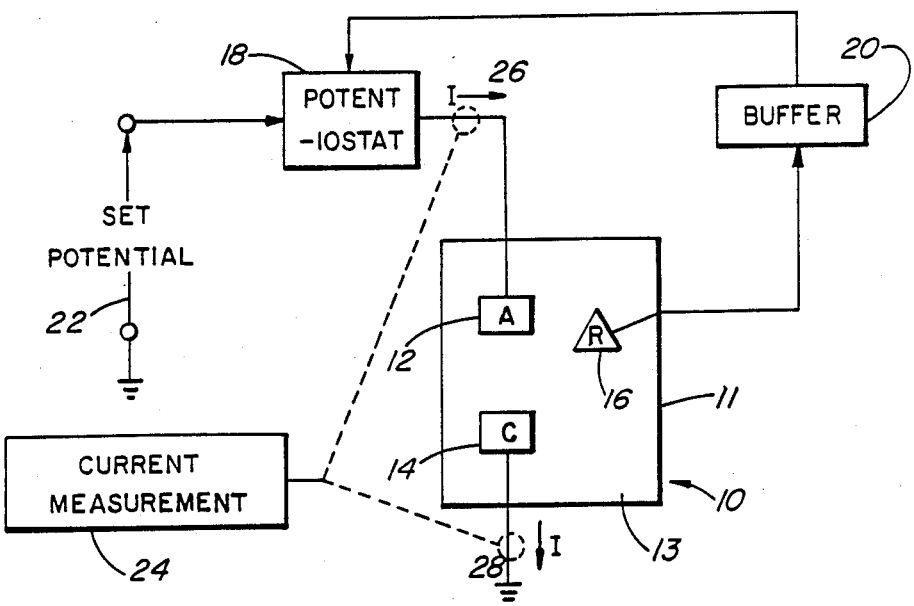
FIG. 1 is a block diagram of a potentiostatic circuit for a single cathode configuration used in the prior art.

All potentiostatic systems of the prior art can, basically, be reduced to the block diagram as is shown in FIG. 1.

Shown generally at reference numeral 10 is a potentiostatic control apparatus which comprises a test tank 11, an anode 12, cathode 14, and a reference electrode 16. The anode 12, cathode 14 and reference electrode 16 are all immersed in an electrolyte 13, such as sea water.

A potentiostat 18 takes a set potential at 22 and a reference potential at reference electrode 16 as its inputs. In order that negligible current be drawn from the reference electrode, a buffer 20 is placed between the potentiostat 18 and the reference electrode 16. A current 26 flows from the output of the potentiostat 18 through the anode 12, the electrolyte 13, and finally the grounded cathode 14. This produces a potential drop between the reference electrode 16 and the cathode 14 which is equal to the set potential 22.

Current measurement can take place at either the anode 12 or the cathode 14 in a single cathode system such as shown in FIG. 1. This method, however, requires a nonintrusive method of measurement of the demand current 26. This can be achieved by utilizing clip-on current probes 28 attached around the leads leading to the anode 12 or cathode 14.

Figure 2:
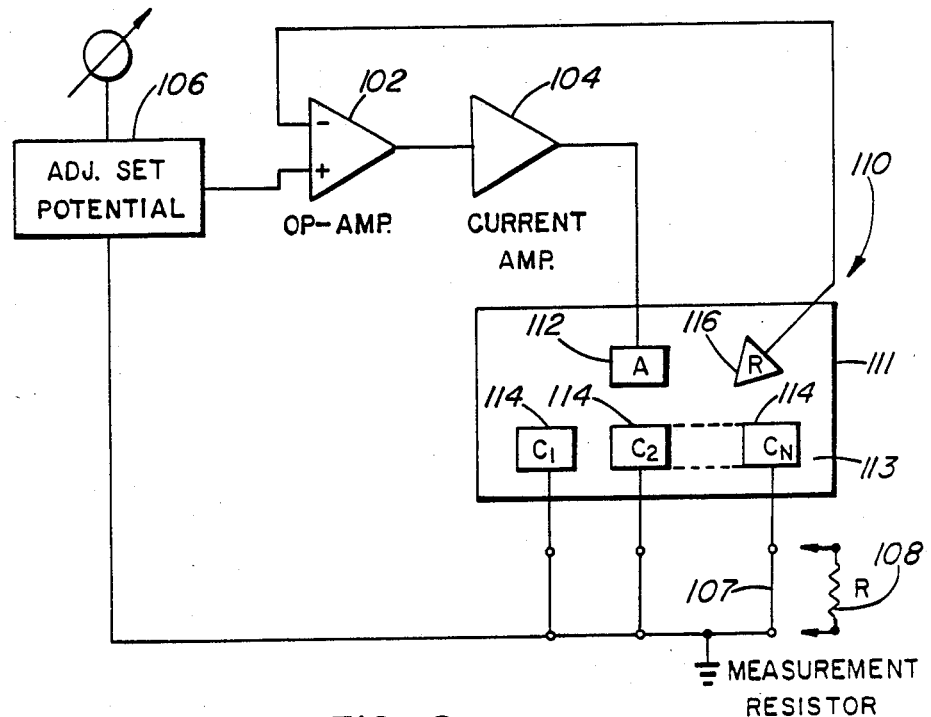
FIG. 2 is a block diagram of a potentiostatic circuit used in the prior art for a multiple cathode configuration.

Referring now to FIG. 2, shown generally at 110 is a multiple cathode configuration used in the prior art. The apparatus comprises a test tank 111, an anode 112, a number of cathodes 114, and a reference electrode 116. The anode 112, cathodes 114, and reference electrode 116 are all immersed in an electrolyte 113. If several potentiostats of the type shown in FIG. 1 or 2 are used in the same test tank, all the reference electrodes will be at approximately the same potential. Thus, it is quite impossible to test a number of cathodes at different set potentials if all of the cathodes are grounded together. The prior art offers a solution to the grounding dilemma by electronically isolating or "floating" the individual potentiostats with respect to each other. This may be accomplished by driving each potentiostat with its own floating power supply. In FIG. 2, the adjustable set potential 106, op-amp 102 and current amplifier 104 represent an inexpensive multiple cathode potentiostat system used in the prior art. All the cathodes 114 are shorted through individual connectors 107 to a common local ground. In order to take a current reading, the shorting connector 107 is removed and a low-value (typically 0.1Ω) precision resistor 108 is put in its place. The voltage drop across the resistor is measured using a differential or floating voltmeter and the current calculated using Ohm's law.

It is clear that, as well as being awkward, the introduction of the resistor into the current path introduced an unnecessary, and not always insignificant, error.

Figure 3:
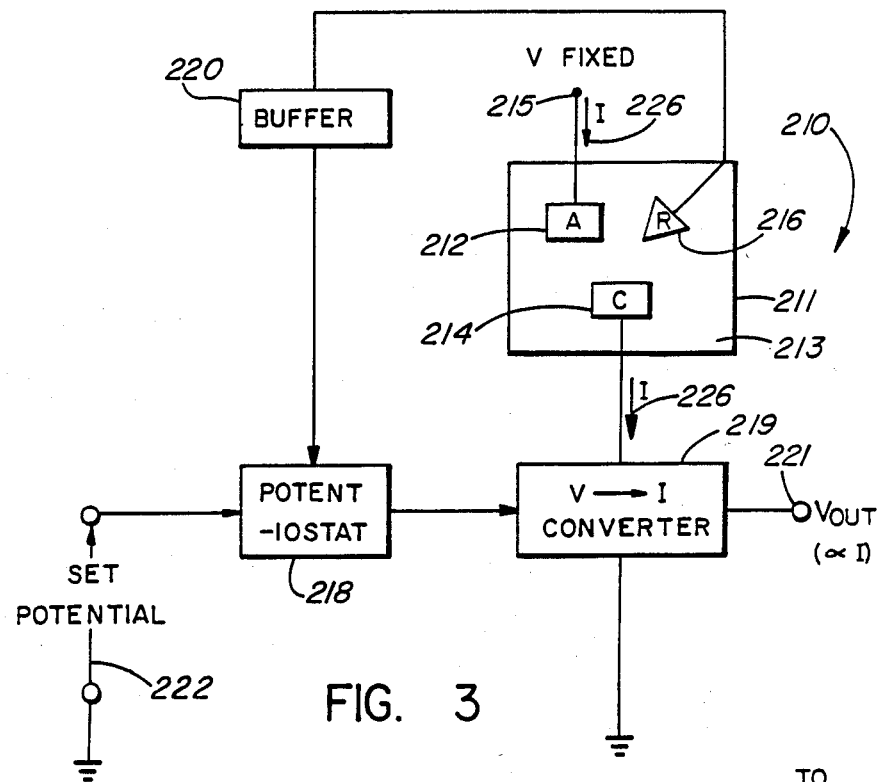
FIG. 3 is a block diagram of the potentiostatic circuit used in the present invention.

Referring now to FIG. 3, reference numeral 210 shows a block diagram configuration of the Long Term Current Demand system in accordance with the present invention. The LTCD system of the present invention employs a novel method to achieve the potentiostatic function.

As was described earlier, the potentiostat design of the prior art was "driving" the ionizing current through the variable potential anode to the grounded cathodes.

In the present invention the cathode 214 is ungrounded and the ionizing current 226 is "drawn" from the fixed potential anode 212 through an electrolyte 213 to the cathode 214.

The apparatus comprises an anode 212, a cathode 214, and a reference electrode 216 all immersed in electrolyte 213 in test tank 211. A fixed potential 215 is applied at the anode 212. The reference electrode 216 is connected to the potentiostat 218 via a buffer 220 so that negligible current is drawn from the reference electrode. Potentiostat 218 is responsive to a set potential 222 and a reference potential from said reference electrode 216 such that the algebraic difference between set potential 222 and the reference potential at said reference electrode 216 causes a variation of the current 226 drawn from the cathode 214 which gives an indication of the corrosive action affecting the cathode 214. The voltage output 221 of voltage to current converter 219 is directly proportional to the current 226 drawn from the cathode.

Using the present invention it is possible to design a multiple-potential, multiple-cathode potentiostatic control system which requires only two power supplies: one to offset the anode to some fixed potential and one to supply the power requirements for the LTCD system electronics. The system may be composed of any number of potentiostats, each with its own adjustable set potential, all using the same power supply. Each of the potentiostats may control the potential of any number of cathodes. Furthermore, each cathode is provided with its own individual potentiostatic current control.

Figure 4:
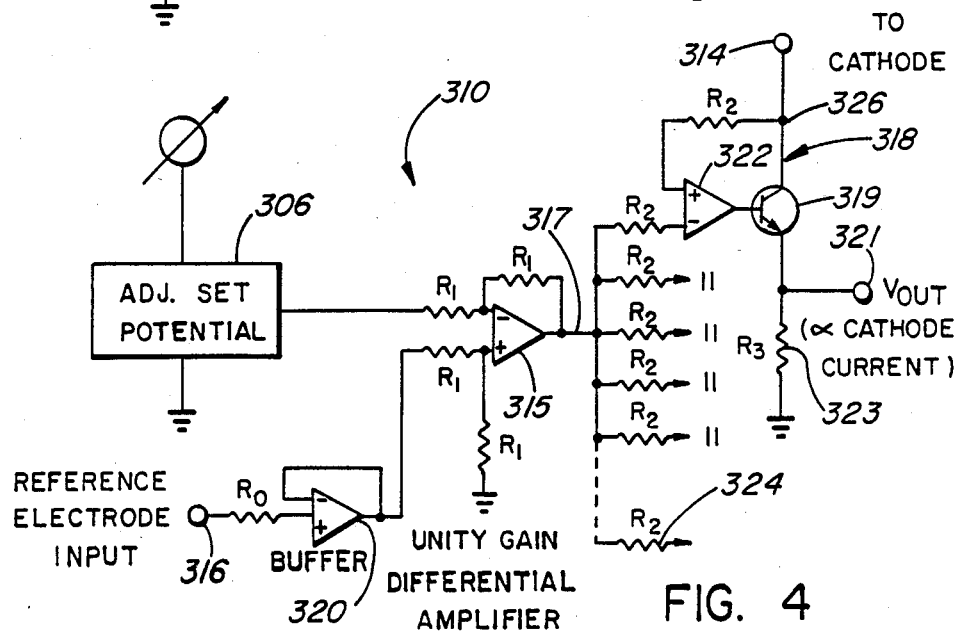
FIG. 4 is a detailed schematic of the potentiostatic circuit used in the present invention for a multiple cathode configuration.

A more detailed schematic diagram of one example of a circuit used to implement the present invention is shown in FIG. 4. The reference electrode output voltage 316 is fed to a unity gain follower or buffer 320 which has a very high input impedance and a very low output impedance, thus the buffer 320 will not load the reference electrode 216 as shown in FIG. 3. The buffered signal is fed to the non-inverting input of a unity gain differential amplifier 315. The set potential 306, also buffered (not shown), is obtained from a temperature-compensated voltage reference (not shown). The set potential 306 is continuously user-adjustable by means of a multi-turn trimpot. The set potential 306 is fed to the inverting input of the unity gain differential amplifier 315. The output 317 of amplifier 315 is the algebraic difference of the reference potential and set potential.

The actual potentiostatic current control is performed by the op-amp-transistor pair shown generally at 318. Since the transistor 319 performs a signal inversion of the op-amp output, the inverting input of the op-amp 322 becomes the non-inverting input of the op-amp-transistor pair 318. The output 317 of the differential amplifier 315 is fed to the non-inverting input of the op-amp-transistor pair 318 or inverting input of op-amp 322. The cathode voltages at 314 are fed to the inverting input of the op-amp-transistor pair 318 or non-inverting input of the op-amp 322. In this configuration, the op-amp-transistor pair will draw whatever current 326 is necessary to maintain the cathode 314 at a voltage equivalent to the reference potential less the set potential. For a multiple cathode configuration, corresponding op-amp-transistor pairs can be provided at 324 for each cathode used. The current 326 drawn by the potentiostat can be measured at 321 by using a precision resistor 323 providing a voltage drop proportional to the current drawn. This integral precision resistor 323 provides the means to easily and unobtrusively measure the cathode currents 326.

The individual electronic functions of the circuit can be performed by any number of readily available integrated circuits (IC's) and semiconductors. In this particular system, a µA723 was chosen for the set potential circuit because it is an inexpensive, readily available, proven IC with a stable, temperature compensated voltage reference (not shown). The op-amps chosen for the system are µA714's which have a very low input-offset (error) voltage and temperature drift. The transistor chosen is a MPS-U45 power Darlington transistor. Because of its high current gain, essentially all the current leaving the emitter is cathode current. A 49.9Ω precision (1%) resistor was chosen to provide 10 volts drop at a cathode current of 200 mA. For low current applications, the precision 49.9Ω resistor should be replaced by a 4.99K precision (1%) resistor. The MPS-U45 transistor should be replaced by a VN10KM MOSFET to inhibit current flow from the 714 op-amp to the 4.99K Ω precision resistor.

It is evident from the foregoing that a method and one form of apparatus to carry out that method have been described within the context of this invention. Other variants will be seen by persons knowledgeable in this art. It is intended to encompass in the claims below all such variants which embrace changes and modifications to the preferred embodiments described herein, and which will be apparent to those persons skilled in this art.

The embodiments of the invention in which an exclusive property or privilege is claimed are defined as follows:

1. A method of measuring long term current demand in a metal plate cathode to determine parameters of cathodic protection for said plate, said plate cathode forming part of an electrical circuit in an apparatus, said apparatus having an anode and a reference electrode wherein the anode, reference electrode, and cathode are immersed in an electrolyte, comprising the steps of:
    applying a fixed potential to said anode;
    measuring a reference potential at said reference electrode; and
    drawing a current directly through the cathode and said anode by means of a potentiostatic control, said potentiostatic control being responsive to an established set potential and said measured reference potential at said reference electrode, wherein the algebraic difference between said set potential and said reference potential causes a variation of said current drawn through said cathode which is indicative of corrosive action affecting said cathode.

2. A method of measuring long term current demand in groups of metal plate cathodes to determine parameters of cathodic protection for each plate of said groups, said groups forming part of an electrical circuit in an apparatus, said apparatus having one anode only and one reference electrode per each said group of cathodes wherein the anode, reference electrodes, and groups of cathodes are immersed in an electrolyte, comprising the steps of:
    applying a fixed potential to said anode;
    measuring a reference potential at each of said reference electrodes; and
    drawing a current directly through each of said cathodes in each of said groups from said anode by means of a potentiostatic control, said potentiostatic control being responsive to an established set potential for each group of plate cathodes and said measured reference potential at each associated said reference electrode, whereby the algebraic difference between said set potential and said reference potential in each group causes a variation of said current drawn from each of said cathodes in said group which is indicative of corrosive action affecting each of said cathodes.

3. An apparatus for measuring long term current demand in metal plate cathodes to determine parameters of cathodic protection for said plates, said plate cathodes forming part of an electrical circuit having an anode and a reference electrode wherein the anode, reference electrode, and cathodes are immersed in an electrolyte, comprising:
    means to apply a fixed potential to said anode; means to measure a reference potential at said reference electrode; and
    potentiostatic control means operable to draw current directly through each of said cathodes from said anode in said electrolyte, said potentiostatic control being responsive to an established set potential and said measured reference potential at said reference electrode, wherein the algebraic difference between said set potential and said reference potential causes a variation of said current drawn through each of said cathodes which is indicative of corrosive action affecting each of said cathodes.

4. An apparatus as defined in claim 3 wherein the potentiostatic control means consist of an operational-amplifier/transistor pair, said operational-amplifier/transistor pair having an op-amp connected to a transistor, said op-amp having inverting and non-inverting inputs and an output, said inverting input being responsive to said algebraic difference, said non-inverting input being responsive to said cathode potential, said output of said op-amp being connected to the base of said transistor of said op-amp-transistor pair, said transistor having the collector connected to said cathode and said non-inverting input of said op-amp and the emitter connected to ground via a resistor, said resistor having a voltage drop proportional to said current drawn through said cathode, said op-amp-transistor pair drawing current necessary to maintain said cathode at a voltage equivalent to said reference potential less said set potential.

* * * * *